United States Patent [19]

Rammler et al.

[11] Patent Number: 5,281,532
[45] Date of Patent: Jan. 25, 1994

[54] PSEUDOMAS HOSTS TRANSFORMED WITH BACILLUS ENDOTOXIN GENES

[75] Inventors: David H. Rammler, Woodside; Frank H. Gaertner, San Diego; David L. Edwards, Del Mar, all of Calif.

[73] Assignee: Mycogen Corporation, San Diego, Calif.

[21] Appl. No.: 980,129

[22] Filed: Nov. 23, 1992

Related U.S. Application Data

[60] Continuation of Ser. No. 595,718, Oct. 9, 1990, abandoned, which is a continuation of Ser. No. 115,293, Nov. 2, 1987, abandoned, which is a division of Ser. No. 826,404, Feb. 5, 1986, abandoned, which is a continuation-in-part of Ser. No. 774,120, Sep. 9, 1985, abandoned, which is a continuation-in-part of Ser. No. 717,207, Mar. 28, 1985, abandoned, which is a continuation-in-part of Ser. No. 517,764, Jul. 27, 1983, abandoned.

[51] Int. Cl.$^5$ .............................. C12N 1/21
[52] U.S. Cl. .................. 435/252.34; 435/69.1; 435/172.3; 435/320.1; 424/93 N; 536/23.71
[58] Field of Search .................. 424/93 L, 93 N; 435/69.1, 172.3, 320.1, 254, 252.3; 536/23.71

[56] References Cited

PUBLICATIONS

Faust et al, 1981, In Genetic Engineering in the Plant Sciences, N. J. Panopoulos (ed), Praeger, N.Y., pp. 225-252.
Bogdasarian et al. 1981 *Gene* 16:237-241.
Hinnen et al 1978 *PNAS* 75(4):1929-1933.
Held et al 1982 *PNAS* 79:6065-6069.
N. J. Panopoulos, 1986, Tactics and Feasibility of Genetic Engineering of Biocontrol Agents; In: Fokkema and van den Heuvel (eds), Microbiology of the Phyllosphere, Cambridge Univ. Press, pp. 312-332.

*Primary Examiner*—Richard A. Schwartz
*Assistant Examiner*—J. LeGuyader
*Attorney, Agent, or Firm*—Saliwanchik & Saliwanchik

[57] ABSTRACT

Novel biological pesticides are prepared by introducing into a microorganism the genetic capability to produce a heterologous pesticide, wherein the microorganism is capable of proliferating in the rhizosphere or phylloplane in competition with wild-type microorganisms. A gene capable of expressing a polypeptide is introduced into the microorganism under conditions which allow for stable maintenance and expression of the gene, without significantly diminishing the ability of the microorganism to compete in the environment. Preferred microorganisms provide for the maintenance and protection from degradation of the polypeptide pesticide.

2 Claims, No Drawings

PSEUDOMAS HOSTS TRANSFORMED WITH BACILLUS ENDOTOXIN GENES

CROSS REFERENCE TO RELATED APPLICATIONS

This application is a continuation of Ser. No. 07/595,718, filed Oct. 9, 1990, now abandoned, which is a continuation of Ser. No. 07/115,293, filed Nov. 2, 1987, now abandoned, which is a division of Ser. No. 826,404, filed Feb. 5, 1986, now abandoned, which is a continuation in-part of our application Ser. No. 774,120, filed on Sep. 9, 1985, now abandoned, which is a continuation-in-part of our application Ser. No. 717,207, filed on Mar. 28, 1985, now abandoned, which is a continuation-in-part of our application Ser. No. 517,764, filed on Jul. 27, 1983, now abandoned.

BACKGROUND OF THE INVENTION

A number of naturally-occurring microorganisms produce polypeptide pesticides, which pesticides are capable of controlling the proliferation of many agricultural pests. For a number of reasons these naturally produced pesticides have not found widespread commercial exploitation, despite their ecological desirableness. In many cases, the organism is difficult to grow, the cost of the pesticide is high, the residual activity of the pesticide in the environment is relatively low, and in individual instances, there are additional drawbacks.

Microorganisms, like most living things, occupy specialized niches in the environment. A rather comprehensive review, entitled "Ecology and Epidemiology of Foliar Bacterial Plant Pathogens," is found in Annual Review of Phytopathology (1983, Hirano, S. S. and Upper, C. D. 21:243–69). Survivability is usually adversely affected when an organism is introduced into an exotic environment. Such is the case with naturally-occurring microorganisms that produce pesticides. In order to be effective as pesticides, the naturally-occurring microorganisms and/or their products must be introduced into exotic environments and, therefore, have insufficient residual activity. However, the potency of the pesticides and their ecological desirableness make them attractive candidates for commercial exploitation, if the detractions to their use could be removed or at least ameliorated.

There is, therefore, substantial interest in finding economical ways to produce these pesticides, to deliver them to the field in a bioactive form, and to enhance and prolong their activity in the environment.

Bulla et al., (1981) J. Biol. Chem. 254:3000–3004, describe the proteinaceous parasporal crystal toxin from B. thuringiensis var. kurstaki. Held et al., (1982) Proc. Natl. Acad. Sci. USA 79:6065–6069, describe the cloning of the gene for proteinaceous parasporal crystal toxin into E. coli and B. subtilis. See also, Schnepf et al. ibid (1981) 78:289–294. Wong et al., (1983) J. Biol. Chem. 258:1960–1967, describe the transcriptional regulatory signals of the B. thuringiensis toxin gene. Klier et al., (1982) EMBO 1:791–799, describe the cloning and expression of a Bt toxin gene. U.S. Pat. No. 4,265,880 describes embedding live insecticidal pathogens in a coacervate microbead.

BRIEF SUMMARY OF THE INVENTION

Novel microorganisms are provided, by modifying organisms capable of occupying, surviving and proliferating in the phytosphere of plants. The microorganisms are modified by introduction of one or more genes capable of expression in the microorganism of a pesticide, particularly an insecticide. The Preferred microorganisms grow with the plant, continually produce pesticide and protect the pesticide from environmental degradation. These novel microorganisms (biological packages) serve to deliver pesticides to and maintain their activity in the phytosphere of plants.

DETAILED DESCRIPTION OF THE INVENTION

Modified microorganisms containing the genetic capability for expression of polypeptide pesticides, methods for producing the modified microorganisms and methods for using the microorganisms are described. Microorganisms are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of plant leaves) and/or the rhizosphere (the soil surrounding plant roots) of a wide variety of important crops. These microorganisms include bacteria, algae, and fungi. Of particular interest are microorganisms, such as bacteria e.g., genera Pseudomonas, Erwinia, Serratia, Xanthomonas, Streptomyces, Rhizobium, Rhodopseudomonas, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms. The above microorganisms are all readily available from natural sources or established culture repositories, such as NRRL and ATCC.

Among naturally-occurring toxins are the polypeptide crystal toxins of *B. thuringiensis* var. kurstaki, active against lepidoptera; B.t. var. israelensis, active against mosquitoes; B.t. M-7, active against coleoptera; and *B. sphaericus,* active against mosquito larvae. Other toxins include those of entomopathogenic fungi, such as beauverin of *Beauveria bassiana* and destruxins of Metarrhizium spp.; or the broad spectrum insecticidal compounds, such as the avermectins of *Streptomyces avermitilus.* Cultures exemplifying the above are as follows:

Bacillus thuringiensis var. kurstaki HD-1—NRRL B-3792; disclosed in U.S. Pat. No. 4,448,885
Bacillus thuringiensis var. israelensis—ATCC 35646
Bacillus thuringiensis M-7—NRRL B-15939

The following *B. thuringiensis* cultures are available from the United States Department of Agriculture (USDA) at Brownsville, Tex. Requests should be made to Joe Garcia, USDA, ARS, Cotton Insects Research Unit, P.O. Box 1033, Brownsville, Tex. 78520 USA.

*B. thuringiensis* HD2
*B. thuringiensis* var. finitimus HD3
*B. thuringiensis* var. alesti HD4
*B. thuringiensis* var. kurstaki HD73
*B. thuringiensis* var. sotto HD770
*B. thuringiensis* var. dendrolimus HD7
*B. thuringiensis* var. kenyac HD5
*B. thuringiensis* var. galleriae HD29
*B. thuringiensis* var. canadensis HD224
*B. thuringiensis* var. entomocidus HD9
*B. thuringiensis* var. subtoxicus HD109
*B. thuringiensis* var. aizawai HD11
*B. thuringiensis* var. morrisoni HD12
*B. thuringiensis* var. ostriniae HD501
*B. thuringiensis* var. tolworthi HD537
*B. thuringiensis* var. darmstadiensis HD146
*B. thuringiensis* var. toumanoffi HD201
*B. thuringiensis* var. kyushuensis HD541
*B. thuringiensis* var. thompsoni HD542
*B. thuringiensis* var. pakistani HD395
*B. thuringiensis* var. israelensis HD567
*B. thuringiensis* var. indiana HD521
*B. thuringiensis* var. dakota
*B. thuringiensis* var. tohokuensis HD866
*B. thuringiensis* var. kumanotoensis HD867
*B. thuringiensis* var. tochigiensis HD868
*B. thuringiensis* var. colmeri HD847
*B. thuringiensis* var. wuhanensis HD525
*Bacillus cereus*--ATCC 21281
*Bacillus moritai*--ATCC 21282
*Bacillus popilliae*--ATCC 14706
*Bacillus lentimorbus*--ATCC 14707
*Bacillus sphaericus*--ATCC 33203
*Beauveria bassiana*--ATCC 9835
*Metarrhizium anisopliae*--ATCC 24398
*Metarrhizium flavoviride*--ATCC 32969
*Streptomyces avermitilus*--ATCC 31267

The toxin need not be the same as a naturally occurring toxin. Polypeptide toxins may be fragments of a naturally-occurring toxin; expression products of deletion, transversion or transition mutations, where two or fewer number percent of the amino acids may be changed; or a repetitive sequence capable of processing by the intended pest host. In addition, fusion products may be prepared where one, five or more amino acids are provided at the N-terminus to provide, for example, reduced proteolytic degradation of the toxin(s). In some instances, a plurality of the same or different toxins may be encoded and expressed, where processing sites may be introduced between each toxin moiety in the polytoxin.

A wide variety of ways are available for introducing the genie expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will occur only after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct or may be combined as a separate DNA fragment with the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin producing host, so that it may effectively compete with the wild-type microorganisms and stably occupy a niche in the environment of the vegetation to be protected.

Where no functional replication system is present, the construct will also include a sequence of at least 50 bp, preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that the toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898; 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069 and Bagdasarian et al., (1981) Gene 16:237, and U.S. Pat. Nos. 4,356,270; 4,362,817 and 4,371,625.

The structural gene expressing the toxin may be isolated from its host in a variety of ways. Where the structural gene has been described in the literature, and sequenced and/or restriction mapped, and a sequence is available for preparing a probe, various techniques exist for preparing a library, determining which clone(s) in the library contains a complementary sequence to the probe, isolating the DNA fragment containing the desired structural gene and then modifying the fragment, as appropriate. Modification may include complete or partial digestion with one or more restriction enzymes, resection, primer repair, in vitro mutagenesis, or the like, where the entire structural gene, or a fragment having toxin activity is isolated.

The structural gene may then be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

While several polypeptide toxins are known which are heterologous to the ultimate host (by heterologous is intended products not normally produced by the ultimate host), the preferred polypeptide toxins are related to the naturally-occurring proteinaceous parasporal crystal toxins produced by wild-type *B. thuringiensis*. One or more structural genes encoding for different polypeptide toxins may be introduced into a host, either on the same or different compatible plasmids or under conditions of integration into the host genome.

The toxins produced in the heterologous host need not be identical to the toxin as prepared by its native host, even where it shares the same polypeptide sequence, since the toxin may be subject to varying degrees of glycosylation, depending upon the particular host.

The transformants may be isolated in accordance with conventional ways, usually employing a selection technique, which allows for selection of the desired organism as against unmodified organisms or transferring organisms, when present. The transformants may then be tested for pesticidal activity, particularly insecticidal activity. Various insect pests include diptera (flies and mosquitoes), lepidoptera (moths and butterfly larvae), coleoptera (beetle larvae and adults), and the like. For the assay of insecticidal activity the larvae of the tobacco hornworm, *Manduca sexta*, or cabbage looper, *Trichoplusia ni* may be employed according to the procedures described by Schnepf et al., supra.

Preferred hosts, particularly those in the phytosphere, will have certain characteristics which enhance the environmental stability of the toxins in the host. Protective qualities include a low level of proteolytic degradation, thick cell walls, pigmentation, and the like. Other characteristics of interest for the host include leaf affinity, lack of mammalian toxicity, attractiveness to pests for ingestion, ease of handling and storage, rate of proliferation in the field, competitiveness, and the like.

In the field applications, the transformant strain will be applied to its natural habitat, such as the rhizosphere or phylloplane of the plant to be protected from the pest. The transformant strain will grow in its natural habitat, while producing the toxin which will be absorbed and/or ingested by the larvae or adult pest, or have a toxic effect on the ova. The persistence of the microorganisms will provide for long-term protection of the vegetation, although repetitive administrations may be required from time to time. The organism may be applied by spraying, soaking, injection into the soil, seed coating, seedling coating or spraying, or the like. Where administered in the field, generally concentrations of the organism will be from $10^6$ to $10^{10}$ cells/ml, and the volume applied per hectare will be generally from about 0.1 oz to 2 lbs or more. Where administered to a plant part, the concentration of the organism will usually be from $10^3$ to $10^6$ cells/cm$^2$.

In aquatic environments, pesticidal control may be attained below the surface by varying the lipid content of the transformant microorganism strain. It is known that indigenous aquatic algae float due to their lipid content. A variation in lipid content will allow the transformant strain to be distributed at desired depths below the water surface.

For commercial formulations, the organisms may be maintained in a nutrient medium which maintains selectivity and results in a low rate of proliferation. Various media may be used, such as yeast extract or L-broth. Once the organism is to be used in the field, the nonproliferating concentrate may be introduced into an appropriate selective nutrient medium, grown to high concentration, generally from about $10^5$ to $10^9$ cells/ml and may then be employed for introduction into the phylloplane or rhizosphere or for treatment of a plant part, e.g., seed, tuber, and the like; seedling treatment or the like.

The following examples are offered by way of illustration and not by way of limitation.

EXAMPLE 1

Construction of A Heterologous Gene and Transformation into A Suitable Host

A construction began with a clone of *Pseudomonas aeruginosa*, available from Northern Regional Research Laboratories (NRRL B-12127), containing a broad host range shuttle plasmid pRO1614 (J. Bact. [1982] 150:60; U.S. Pat. No. 4,374,200). The plasmid has unique HindIII, BamHI, and SalI and PvuII restriction sites, a PstI insertion, which includes the carbenicillin resistance gene and a *P. aeruginosa* replication system, where the HindIII, BamHi and SalI restriction sites are in a tetracycline resistance gene. The remainder of the plasmid is derived from pBR322. A second plasmid, pSM1-17, has been deposited as a clone of *E. coli* (NRRL B-15976). This deposit was made with the permanent collection of the Northern Regional Research Laboratory, U.S. Department of Agriculture, Peoria, Ill. 61604, USA. Plasmid pSM1-17 confers ampicillin resistance to *E. coli* and contains a 6.8 Kbp HindIII DNA fragment that includes the δ-endotoxin gene from the 50 md plasmid of *Bacillus thuringiensis* HD73. Sufficient toxin is expressed from this gene in *E. coli* to make the intact cells toxic to cabbage loopers. A further modification of the DNA fragment was done to enhance toxin expression and to accomplish expression of toxin in an alternate host, *Pseudomonas fluorescens*. In order to eliminate unwanted DNA from the 6.8 Kbp fragment, pSM1-17 was digested with BamHI to open the circular plasmid at a site nearest to the 5' end of the toxin gene, and was treated with the exonuclease Bal31 to reduce the 6.8 Kbp HindII insert to about 2.9 Kbp. The free ends of the DNA were filled in with Klenow polymerase, BamHI linkers were added, and the linear DNA was ligated to reform the circular plasmid. The resultant vector, pFG270, was digested with XhoI to open the circular plasmid at a site nearest to the 3' end of the toxin gene. SalI linkers were added the plasmid was ligated to its circular form, and the resultant vector, pFG10.6 was amplified in *E. coli*. pFG10.6 was digested completely with SalI and BamHI and the resulting 2.1 Kbp fragment containing the toxin gene was purified by gel electrophoresis and ligated into the BamHI and SalI sites of plasmid pRO1614. The resultant plasmid, pCH2.1, was amplified in *E. coli* and used to transform *Pseudomonas fluorescens* to carbenicillin resistance and the ability to synthesize δ-endotoxin. *Pseudomonas fluorescens* (pCH2.1) was deposited with NRRL and was given the accession number NRRL B-15977. In the following illustrative experiments *P. fluorescens* (pCH2.1) was used in conjunction with controls of untransformed cells.

The culture deposits *E. coli*(pSM1-17)—NRRL B-15976 and *P. fluorescens* (pCH2.1)—NRRL B-15977 were made in the permanent collection of the NRRL repository, to be maintained for at least thirty years. These deposits are available to the public upon the grant of a patent disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

EXAMPLE 2

Testing of Microbes Hosting A Heterologous Gene

In illustrative experiments, two *Pseudomonas fluorescens* strains were used, which had been transformed with plasmid pCH2.1. These strains were used in conjunction with controls of untransformed cells.

Cell pellets from two liter broth cultures of *P. fluorescens* with and without Bt toxin are divided in half. The cells are repelleted in 10 ml of sterile deionized water. Nine ml of this suspension (10E8-10E12 cells/ml) are sprayed on three young lettuce plants. The three sprayed plants are placed in a single enclosed chamber and 50-75 *Trichoplusia ni* larvae are applied to the plants. Plants are considered protected if there is no visible loss of foliage over the observation period.

The following Table 1 indicates the results.

TABLE 1

| Plant Assay 1 - *P. fluorescens* (strain 1)* | | | | |
|---|---|---|---|---|
| Microorganism | Treatment | # Viable Cells/ml | Total # Larvae | Protection |
| *P. fluorescens* | Live | 2.5 × 10E11 | 75 | Not protected |
| *P. fluorescens* + Bt Toxin | Live | 3.1 × 10E11 | 75 | Protected |
| *P. fluorescens* | 1% Lugol's Iodine 4 hrs | 0 | 75 | Not protected |
| *P. fluorescens* + Bt Toxin | 1% Lugol's Iodine 4 hrs | 0 | 75 | Protected |

*Set up
day 1, 25 2-day larvae applied to plants,
day 3, 50 5-day larvae applied to plants,
day 10, observation reported.

In the next study, newly hatched cabbage loopers are placed in a Petri dish containing droplets of the material to be bioassayed. The larvae imbibe the liquid and are then removed to small cups containing larval diet. The larvae are examined after seven days and the total number of animals killed is recorded. The following Table 2 indicates the results.

TABLE 2

| Microorganism | Treatment | # Larvae Killed/ Total | % Larvae Killed | Viable Cell Count/ml |
|---|---|---|---|---|
| Bioassay 1 - *P. fluorescens* (strain 1) | | | | |
| *P. fluorescens* | Live | 0/15 | 0 | 8 × 10E11 |
| *P. fluorescens* + Bt Toxin | Live | 11/18 | 62 | 2.5 × 10E12 |
| *P. fluorescens* | 1% Lugol's 4 hrs | 0/15 | 0 | 0 |
| *P. fluorescens* + Bt Toxin | 1% Lugol's 4 hrs | 8/13 | 62 | 0 |
| Bioassay 2 - *P. fluorescens* (strain 1) | | | | |
| *P. fluorescens* | Live | 0/15 | 0 | 3.7 × 10E11 |
| *P. fluorescens* + Bt Toxin | Live | 3/20 | 15 | 4.5 × 10E11 |
| *P. fluorescens* | 1% Lugol's 4 hrs | 0/15 | 0 | 0 |
| *P. fluorescens* + Bt Toxin | 1% Lugol's 4 hrs | 8/15 | 53 | 0 |
| Bioassay 3 - *P. fluorescens* (strain 2) | | | | |
| *P. fluorescens* | | 6/14 | 30 | 3 × 10E11 |

TABLE 2-continued

| Microorganism | Treatment | # Larvae Killed/Total | % Larvae Killed | Viable Cell Count/ml |
|---|---|---|---|---|
| P. fluorescens + Bt Toxin | | 20/20 | 100 | $3 \times 10E10$ |

EXAMPLE 3

Persistence of Microorganisms on Leaf Surfaces

This example gives the evaluation of various microorganisms for the property of colonizing plant leaves. The better the capacity of the microorganism to colonize leaves, the more useful it is in the subject invention. The following results show, surprisingly, that certain yeasts, for example *Rhodotorula rubra*, are, advantageously, very good colonizers of plant leaves. Thus, these microorganisms are very useful in the practice of the subject invention.

2 μm circle REP3 locus. Recombinant gene expression is driven by the yeast GAL10 gene promoter. The toxin gene can be inserted into YEp51. Other yeast promoters such as alcohol dehydrogenase (Bennetzen, J. L. and Hall, B. D. [1982] J. Biol. Chem. 257:3018; Ammerer, G. in Methods in Enzymology [1983] Vol. 101, p. 192), phosphoglycerate kinase (Derynck, R., Hitzeman, R. A., Gray, P. W. and Goeddel, D. V., in Experimental Manipulation of Gene Expression [1983] p. 247, ed. M. Inouye, Academic Press), triose phosphate isomerase (Alber, T. and Kawasaki, G. [1982] J. Molec. and Applied Genet. 1:419), or enolase (Innes, M. A. et al. [1985] Science 226:21) can be used in a similar mariner with other yeast hosts such as *Rhodotorula rubra*.

It is evident from the above results, that one can introduce a structural gene encoding for a polypeptide toxin into a heterologous host, where the heterologous host is adapted for inhabiting a niche associated with a plant or other pest habitat. The heterologous host is then capable of producing the toxin and providing pro-

HALF-LIFE IN DAYS

| PLANTS | MICROOGANISMS C-1 | C-2 | C-3 | X-1 | X-2 | X-3 | X-4 | X-5 | X-6 | X-7 | X-8 | X-9 | X-10 | X-11 | X-12 | X-13 | X-14 |
|---|---|---|---|---|---|---|---|---|---|---|---|---|---|---|---|---|---|
| lettuce | 2.8 | 10.8 | 1.8 | 68 | 2.8 | 4.8 | 2.9 | 2.4 | 4.5 | 3.2 | 1.8 | 2.9 | 3.2 | 0.6 | 0.6 | 1.0 | 3.9 |
| tomato | | 4.9 | 1.1 | 500+* | | | | | 2.0 | | | 8.7 | | | | | |
| cucumber | | | | 99 | | | | | | | | | | | | | |
| zucchini | | | | 34 | | | | | | | | | | | | | |
| cabbage | | | | 9 | | | | | | | | | | | | | |
| ash | | | | 500+ | | | | | | | | | | | | | |
| birch | | | | 500+ | | | | | | | | | | | | | |
| elder | | | | 500+ | | | | | | | | | | | | | |
| oak | | | | 500+ | | | | | | | | | | | | | |
| plum | | | | 12 | | | | | | | | | | | | | |
| poplar | | | | 7 | | | | | | | | | | | | | |
| sequoia | | | | 500+ | | | | | | | | | | | | | |
| sycamore | | | | 15 | | | | | | | | | | | | | |
| willow | | | | 17 | | | | | | | | | | | | | |

*500+—Cells maintained at 10E5 to 10E6/cm2 for 4 weeks or more. Calculated half-life greater than 500 days.
Cells were sprayed in water at about 10E8/ml. Leaves were washed under standardized conditions and samples were plated for counts and identification of microorganisms. Background counts were from 10E1 to 10E3/cm2. The normalized half-life (NHL) is the expected time, in days, for the starting concentration of cells on the leaf surface to drop 50% (NHL = Log 0.5/−b, where −b is the slope of the linear regression of the decay curve (Log cells/cm2 vs time).
The assays were performed in southern California over a nine-month period from November to July.

| Code | Organism |
|---|---|
| C-1 | Spores of *Bacillus thuringiensis* |
| C-2 | *Pseudomonas fluorescens* leaf isolate |
| C-3 | *Saccharomyces cerevisiae* |
| X-1 | *Rhodotorula rubra* |
| X-2 | *Aureobasidium pullulans* |
| X-3 | Aureobasidium-like isolate from red grapes |
| X-4 | *Cryptococcus albidus* |
| X-5 | *Cryptococcus diffluens* |
| X-6 | *Cryptococcus laurentii* |
| X-7 | Cryptococcus-like isolate from lettuce |
| X-8 | *Rhodotorula aurantiaca* |
| X-9 | *Rhodotorula glutinis* |
| X-10 | *Rhodotorula marina* |
| X-11 | *Saccharomyces pretorienses* |
| X-12 | *Saccharomyces rosei* |
| X-13 | *Sporobolomyces odorus* |
| X-14 | *Sporobolomyces roseus* |

The above results show that *Rhodotorula rubra* (X-1) is the best epiphytic colonizer.

Polypeptide toxins can be expressed in yeast by use of procedures well known in the art. For example, *Bacillus thuringiensis* toxins can be expressed in *Saccharomyces cerevisiae* using plasmids containing the inducible galactose promoter from this organism (Broach, J. R., Li, Y., Wu, L. C. and Jayaram, M. in Experimental Manipulation of Gene Expression [1983] p. 83, ed. M. Inouye, Academic Press). These plasmids are called YEp51 and YEp52 (Broach, J. R. et al. [1983]) and contain the *E. coli* origin of replication, the gene for β-lactamase, the yeast LEU2 gene, the 2 μm origin of replication and the tection to a plant from an insect pest. This indicates that the heterologous host is ingested by the insect pest, as ingested it provides a biocidal amount of the insecticide in active form to the pest, and thus provides protection to the plant.

The subject invention provides a substantial improvement in the utilization of polypeptide toxins, in that the toxins can be introduced into heterologous hosts, which can be economically grown, can be disseminated among vegetation, both on the leaves and in the soil, and will multiply so as to provide the toxin for extended periods of time and in substantially greater amount in the field than originally produced in a manufacturing facility. The host may in addition provide protection to the toxin from environmental deterioration, provide a continuing supply of the toxin, and provide the toxin in a useful biocidal form.

Although the foregoing invention has been described in some detail by way of illustration and example for purposes of clarity of understanding, it will be obvious that certain changes and modifications may be practiced within the scope of the appended claims.

We claim:

1. A live Pseudomonad microorganism capable of occupying the phytosphere of vegetation, said microorganism comprising a heterologous gene derived from a strain of *Bacillus thuringiensis*, said gene is expressed in said microorganism and codes for a pesticidal polypeptide toxin.

2. A Pseudomonad microorganism according to claim 1, wherein said Pseudomonad is *Pseudomonas fluorescens*.

* * * * *

UNITED STATES PATENT AND TRADEMARK OFFICE
CERTIFICATE OF CORRECTION

PATENT NO. : 5,281,532
DATED : January 25, 1994
INVENTOR(S) : David H. Rammler et al It is certified that error appears in the above-indentified patent and that said Letters Patent is hereby corrected as shown below:

Column 2    line 3: Delete "The Preferred" and insert --The preferred--.

Column 3    line 58: Delete "the genie expressing" and insert --the gene expressing--

Column 7    line 48: After "linkers were added" insert --,--.

Column 7    line 51: Delete "with-SalI" and insert --with SalI--.

Column 10   line 13: Delete "mariner" and insert --manner--.

Signed and Sealed this

Sixth Day of December, 1994

Attest:

BRUCE LEHMAN

*Attesting Officer*    *Commissioner of Patents and Trademarks*